United States Patent [19]

Saksena et al.

[11] Patent Number: 4,889,873
[45] Date of Patent: Dec. 26, 1989

[54] INHIBITORS OF SLOW REACTING SUBSTANCE OF ANAPHYLAXIS

[75] Inventors: Anil K. Saksena, Upper Montclair; Jesse K. Wong, Union, both of N.J.; Pietro Mangiaracina, Monsey, N.Y.

[73] Assignee: Schering Corporation, Kenilworth, N.J.

[21] Appl. No.: 121,557

[22] Filed: Nov. 17, 1987

Related U.S. Application Data

[60] Division of Ser. No. 866,996, May 19, 1986, Pat. No. 4,758,594, which is a continuation of Ser. No. 632,143, Jul. 18, 1984, abandoned.

[51] Int. Cl.$^4$ .................. A61K 31/22; C07C 143/90
[52] U.S. Cl. ...................................... 514/560; 514/460; 549/419; 549/420; 562/574; 562/581; 562/595
[58] Field of Search ............... 558/253; 514/460, 560; 549/419, 420; 562/574, 581, 595

[56] References Cited

U.S. PATENT DOCUMENTS

| | | | |
|---|---|---|---|
| 2,602,816 | 7/1952 | Gregory et al. | 260/537 |
| 2,994,662 | 8/1961 | Calhoun et al. | 260/399 |
| 3,217,004 | 11/1965 | Hechenbleikner et al. | 260/429.7 |
| 3,828,086 | 8/1974 | Kenney et al. | 260/413 M |
| 4,061,634 | 12/1977 | Mod et al. | 260/402.5 |
| 4,434,101 | 2/1984 | Cohen et al. | 260/410.1 |
| 4,442,099 | 4/1984 | Nicolaou et al. | 260/501.1 |
| 4,461,775 | 7/1984 | Stanley et al. | 260/402.5 |
| 4,469,705 | 9/1984 | Stanley et al. | 260/402.5 |
| 4,513,005 | 6/1982 | Baker et al. | 260/402.5 |
| 4,533,747 | 8/1985 | Gleason et al. | 560/152 |

FOREIGN PATENT DOCUMENTS

| | | |
|---|---|---|
| 0121350 | 10/1984 | European Pat. Off. . |
| 0153009 | 8/1985 | European Pat. Off. . |
| 57-118555 | 7/1982 | Japan . |
| 2094301 | 9/1982 | United Kingdom . |
| 2101594 | 1/1983 | United Kingdom ............... 260/399 |

OTHER PUBLICATIONS

*J. American Chemical Society*, vol. 79, 1957, pp. 362–365, Koenig et al.
*Chemical Abstracts*, vol. 56, 1962, Subject Index, p. 25N.
Tetrahedron Letters, vol. 23, No. 34, pp. 3463–3466, 1982, E. J. Corey and Dennis J. Hoover.
Proc. Natl. Acad. Sci. U.S.A., vol. 78, No. 5, pp. 3195–3198, May, 1981, Medical Sciences, Jeffrey M. Drazen et al.
Biochemical and Biophysical Research Communications, Dec. 28, 1983, pp. 732–739, John G. Gleason et al.
*Chemical Abstracts*, vol. 89, Abstract No. 130417q, (1978).
*Chemical Abstracts*, vol. 68, Abstract No. 48956x, (1968).
*Chemical Abstracts*, vol. 73, Abstract No. 44807e, (1970).

*Primary Examiner*—Anton H. Sutto
*Attorney, Agent, or Firm*—Gerald S. Rosen; Stephen I. Miller; Henry C. Jeanette

[57] ABSTRACT

Novel compounds and compositions which inhibit SRS-A in mammals are disclosed. Methods for preparing said compounds and compositions and methods for their use for treating allergic reactions, inflammation and for reducing the severity of myocardial infarction resulting from heart attack are disclosed.

Useful intermediates for preparing said compounds are also disclosed.

7 Claims, No Drawings

INHIBITORS OF SLOW REACTING SUBSTANCE OF ANAPHYLAXIS

SUMMARY OF THE INVENTION

The invention sought to be patented in its chemical compound aspect is

A compound having the structural formula I, II or III wherein:

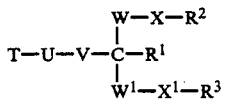

T is straight or branched chain alkyl having from 7–15 carbon atoms which may optionally contain from 1–3 non-cumulative double or triple bonds;
U is $-CH_2CH_2-$, $-CH=CH-$ or $-C\equiv C-$;
V is straight or branched chain alkylene having from 1 to 4 carbon atoms or is a direct bond;
W and $W^1$ may be the same or different and are O or $S(O)_m$ [wherein m is 0, 1 or 2];
X and $X^1$ may be the same or different and are straight or branched chain alkylene having from 2 to 12 carbon atoms which may optionally contain from 1 to 3 non-cumulative double or triple bonds and which may be optionally substituted with the group—$NHR^a$ [wherein $R^a$ is hydrogen, alkyl having from 1 to 6 carbon atoms, $COCF_3$, $CO(CH_2)_2CH(NH_2)CO_2H$, or $SO_2R^b$ (wherein $R^b$ is alkyl having from 1 to 6 carbon atoms or $CF_3$)];
$R^1$ is hydrogen or straight or branched chain alkyl having from 1–6 carbon atoms;
$R^2$ and $R^3$ may be the same or different and are $CH_2OR^c$ [wherein $R^c$ is hydrogen, carboxylic acyl having from 1 to 6 carbon atoms, tetrahydropyran-2-yl or $COCH_2CH_2CO_2H$], CHO, 2-tetrazolyl, $COR^d$ [wherein $R^d$ is hydroxy, alkoxy having from 1 to 6 carbon atoms, $OCH_2OC(O)C(CH_3)_3$, $NHR^e$ (wherein $R^e$ is hydrogen, alkyl having from 1 to 6 carbon atoms or $CH_2CO_2H$)] or $SO_3H$, with the proviso that at least one of $R^2$ and $R^3$ is 2-tetrazolyl or carboxyl;

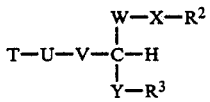

T, U, V, W, X, $R^2$ and $R^3$ are defined above;
Y is straight or branched chain alkylene having from 1 to 12 carbon atoms which may optionally be substituted with the group $OR^c$ [wherein $R^c$ is defined above] and may optionally contain from 1 to 3 non-cumulative double or triple bonds;

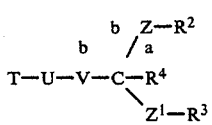

T, U, V, $R^2$ and $R^3$ are defined above;
Z and $Z^1$ may be the same or different and are straight or branched chain alkylene having from 1 to 12 carbon atoms which may optionally contain from 1 to 3 non-cumulative double or triple bonds;
$R^4$ is hydrogen, hydroxyl, or is combined with Z to form a double bond as indicated by the dashed line "a" or a cyclopropyl ring as indicated by the dashed lines "b".

Preferred values for the above-defined substituents are as follows:
T is straight chain alkyl having 7–15 carbon atoms;
U is $-C\equiv C-$;
V is a direct bond;
W is O or S;
$W^1$ is O or S;
X is alkyl having from 2 to 8, more preferably 2 to 6 carbon atoms;
$X^1$ is alkyl having from 2 to 8, more preferably 2 to 6 carbon atoms;
$R^1$ is hydrogen;
$R^2$ is carboxyl;
$R^3$ is carboxyl;
Y is alkyl having from 2 to 6 carbon atoms;
Z is alkyl having from 2 to 6 carbon atoms;
$Z^1$ is alkyl having from 2 to 6 carbon atoms;
$Z^1$ is alkyl having from 2 to 6 carbon atoms;
$R^4$ is hydrogen, hydroxyl or is combined with Z to form a double bond.

A preferred subgenus of compounds is a compound having structural formula I, II or III wherein the substituents T-U-V- are combined to form the n-1-tetradecyn-1-yl group, i.e. $n-C_{12}H_{25}C\equiv C-$.

An additional preferred subgenus of compounds is a compound having structural formula I, II or III wherein the substituents $R^2$ and $R^3$ may be the same or different and are $COR^d$ wherein $R^d$ is defined above.

Preferred species of the invention are those having the following names:
butanoic acid, 4,4'-[2-pentadecynylidenebis(oxy)]bis-;
hexanoic acid, 6,6'-[2-pentadecynylidenebis(oxy)]bis-;
(±)-pentanoic acid, 4,4'-[2-pentadecynylidenebis(oxy)]-bis-;
(±)-heptanoic acid, 6,6'-[2-pentadecynylidenebis(oxy)]-bis-;
butanoic acid, 4-[[1-(4-hydroxybutoxy)-2-pentadecynyl]oxy]-;
butanoic acid, 4,4'-[2-pentadecynylidenebis(thio)]bis-;
hexanoic acid, 6,6'-[2-pentadecynylidenebis(thio)]bis-;
butanoic acid, 4,4'-[tridecylidenebis(oxy)]bis-;
butanoic acid, 4,4'-[pentadecylidenebis(oxy)]bis-;
(±)-hexanoic acid, 5,5'-[2-pentadecynylidenebis(oxy)]-bis-;
(±)-6-[(2-carboxyethyl)thio]-7-eicosynoic acid;
(±)-6-[(3-carboxypropyl)thio]-7-eicosynoic acid;
(+) and (−)-6-[(5-carboxypentyl)thio]-7-eicosynoic acid;
(±)-6-[(5-carboxypentyl)oxy]-7-eicosynoic acid;
potassium 6-[[2-[(trifluoroacetyl)amino]ethyl]thio]-7-eicosynoate;
(±)-6-[(2-amino-3-hydroxy-3-oxopropyl)thio]-7-eicosynoic acid, dipotassium salt;
(±)-6-[[2-carboxy-2-[(trifluoroacetyl)amino]ethyl]thio]-7-eicosynoic acid;
6-hydroxy-6-(1-tetradecynyl)undecanedioic acid;
6-(1-tetradecynyl)undecanedioic acid;
6-(1-tetradecynyl)undec-5(E) and (Z)ene dioic acids;
(±)-pentanoic acid, 4,4'-[2-pentadecynylidenebis(thio)]bis-;
6-tetradecyl-6-hydroxy-undecanedioic acid;
2-butynoic acid, 4,4'-[2-pentadecynylidenebis(oxy)]bis-;

methanesulfonamide, N,N'-[2-pentadecynylidenebis[oxy(5-methyl-5,1-pentanediyl)]]bis-; and hexanoic acid, 5-[[1-[(5-amino-1-methyl-5-oxopentyl)oxy]-2-pentadecynyl]oxy].

The invention sought to be patented in its pharmaceutical composition aspect is a composition which comprises a compound having the structural formula I, II or III in combination with a pharmaceutically acceptable carrier.

The invention sought to be patented in its first pharmaceutical method aspect is a method for treating allergic reactions in a mammal, which comprises administering the above-defined composition to said mammal.

The invention sought to be patented in its second pharmaceutical method aspect is a method for treating inflammation in a mammal, which comprises administering the above-defined composition to said mammal.

The invention sought to be patented in its third pharmaceutical method aspect is a method for reducing the severity of myocardial infarction resulting from heart attack in a mammal, which comprises administering the above-defined composition to said mammal.

DESCRIPTION OF THE INVENTION

The compounds of the invention having structural formula I may be prepared by reacting a compound having structural formula X with a compound having the structural formula XI, $$T-U-V-CR^1(OR')_2 \qquad X$$

$$HWXR^2 \qquad XI$$

wherein T, U, V, W, X, $R^1$ and $R^2$ are as defined herein and R' is any convenient alkyl group, preferably ethyl. The carbonyl compound which corresponds to compound X, i.e., $T-U-V-COR^1$, may optionally be utilized in this reaction in place of compound X. This reaction is preferably carried out under conditions whereby the reaction-produced alcohol, R'OH, or water is continuously removed as it is formed. This continuous removal may be accomplished by azeotropic distillation using a solvent such as benzene or toluene. The reaction proceeds best when catalyzed by acid, e.g. p-toluenesulfonic acid may be utilized; When an excess (i.e. 2 equivalents or more) of reactant XI is utilized, compounds having structural formula I wherein $-W-X-R^2$ and $-W^1-X^1-R^3$ are equivalent will be produced. When compounds having structural formula I wherein $-W-X-R^2$ and $-W^1-X^1-R^3$ are different are desired, the reaction may be accomplished in two separate steps utilizing one equivalent of the desired reactant, XI, in each step. In an additional method, a compound having structural formula I where W and $W^1$ are both oxygen may be treated with one equivalent of a compound having structural formula XI wherein W is sulfur to thereby displace either the $W-X-R^2$ or the $W^1-X^1-R^3$ substituent. For purposes of this procedure, the $W-X-R^2$ and $W^1-X^1-R^3$ substituents of starting compound I should ideally be equivalent. This procedure is conveniently carried out using an acid catalyst such as boron trifluoride. Compounds having structural formula I wherein W and $W^1$ are sulfur may be oxidized to the corresponding sulfoxide or sulfone by known procedures.

Compounds having structural formula II may be prepared from a compound having formula XII, wherein T, U, V, Y and $R^3$ are defined above.

$$T-U-V-CH(OH)YR^3 \qquad XII$$

Compounds having structural formula II wherein W is sulfur may be prepared by first converting the hydroxyl substituent of compound XII to a more readily displacable substituent, e.g. the methane sulfonic acid ester, XIII, $$T-U-V-CH(OSO_2CH_3)YR^3 \qquad XIII$$

or to the corresponding bromo or an activated phosphorous substituent.

The conversion of XII to XIII may be carried out by treating XII with methane sulfonyl chloride under standard conditions. Compound XIII may then be treated with a compound having structural formula XIV.

$$HS-X-R^2 \qquad XIV$$

using known conditions to produce the desired compounds having structural formmula II wherein W is sulfur. The sulfur atom may thereafter be oxidized to the corresponding sulfoxide or sulfone by known procedures if desired.

Compounds having structural formula II wherein W is oxygen may be prepared from compound XIII in a similar manner by using the alcohol XV $$HO-X-R^2 \qquad XV$$

Alternatively, compound XII may be converted to compound II wherein W is oxygen by direct alkylation on the hydroxyl oxygen atom. Thus, for example, XII may be treated with a base such as sodium hydride to form the corresponding sodium salt of the alcohol, XVI.

$$T-U-V-CH(ONa)YR^3 \qquad XVI$$

This salt may next be treated with a halide compound, for example, an iodo compound such as $IXR^2$ to produce the compounds having structural formula II wherein W is oxygen.

Compounds having structural formula III may be prepared by reacting an anion derived from a compound having structural formula XVII, $$T-U-V-H \qquad XVII$$

i.e. compound XVIII $$T-U-V^-M+ \qquad XVIII$$

wherein M+ is a metal cation such as the lithium cation, or an equivalent complex metal cation, e.g. MgBr+ with a carbonyl compound having structural formula XIX

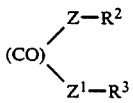

XIX using known procedures. This reaction will produce compounds having structural formula III wherein $R^4$ is a hydroxyl group. This tertiary alcohol function may thereafter be converted to other $R^4$ substituents by known methods if desired. For example, treatment of the tertiary alcohol with diethylaminosulfur trifluoride will produce the corresponding compound wherein $R^4$ is fluorine. The tertiary alcohol may be dehydrated to produce a compound wherein $R^4$ and Z are combined to form a double bond, i.e. a compound having structural formula III wherein the dashed line "a" indicates a double bond. This double bond compound may be reduced to produce the compounds wherein $R^4$ is hydrogen, or it may be reacted with methylene carbene to produce the corresponding cyclopropyl compounds, i.e. a compound having structural formula III wherein the dashed lines "b" indicate the completion of a cyclopropyl ring.

In certain of the above-described reactions certain substituents may have to be protected in order to avoid unwanted reactions. Thus, for example, certain of the $R^2$ and $R^3$ substituents may be protected by art recognized methods. In addition, certain of the groups, $R^2$ and $R^3$ may be modified, if desired, by known procedures. Thus, for example, a compound wherein $R^2$ is $CH_2OH$ may be converted to a compound wherein $R^2$ is $CO_2H$ by oxidation or to a compound wherein $R^2$ is $CH_2OCOCH_3$ by acylation.

For purposes of completeness, the following abbreviated reaction sequence is utilized to exemplify a process for performing selective reactions where multiple sites of unsaturation are present. Other such sequences are known in the art.

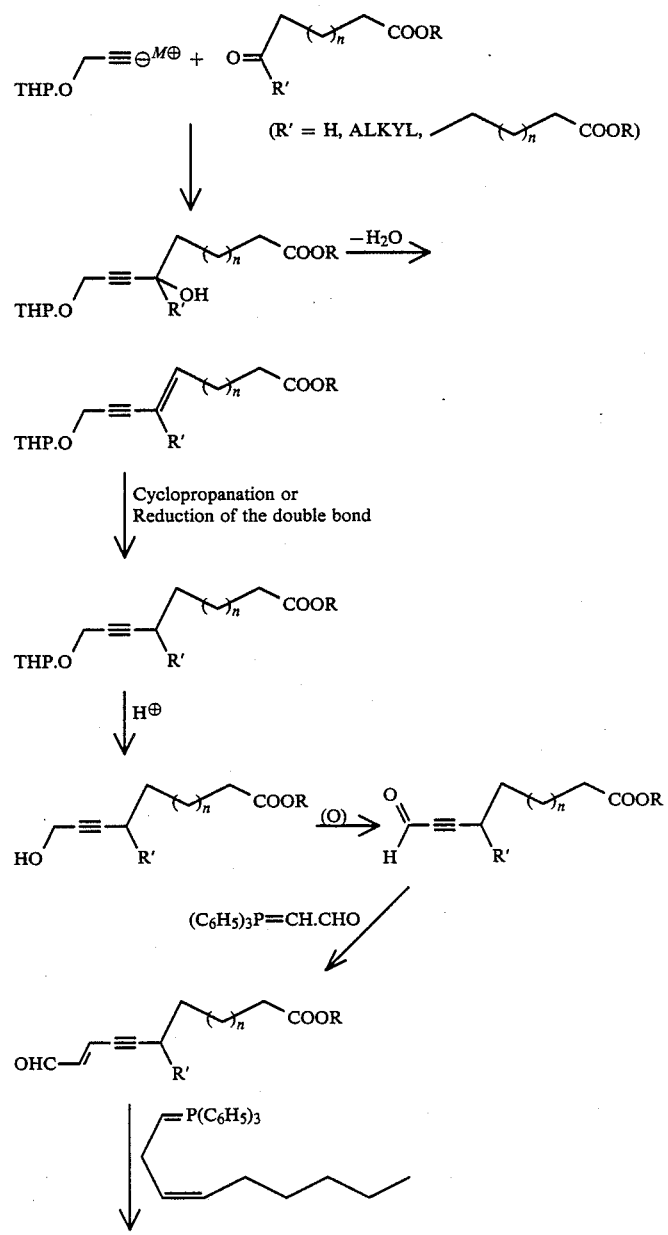

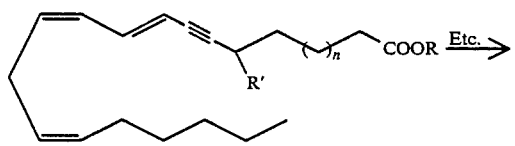

In the above abbreviated reaction sequence, THP indicates the 2-tetrahydropyranyl radical. Double bonds can be regiospecifically included or excluded by proper choice of carbon to carbon bond forming reactions and reagents which will be known to those skilled in the art.

The above-described starting materials are either known compounds or preparable from known compounds by art-recognized methods.

Thus, compound X is an acetal or ketal, which compounds are preparable from the corresponding aldehyde or ketone by well known methods. In an alternate method, a compound such as XX may be reacted with an orthoester such as ethyl orthoacetate by known methods to produce the acetal XXI.

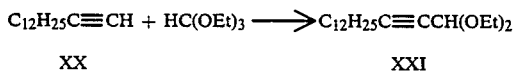

|     |     |
| --- | --- |
| XX  | XXI |

Compounds having structural formula XII are secondary alcohols which may be prepared, for example, by the reaction of a Grignard reagent such as XXII with an aldehyde such as XXIII.

T—U—V—MgBr        XXII

OHCYR$^3$            XXIII

Known equivalent reactants to XXII such as lithium reagents, e.g. XXIV, may also be utilized.

           XXIV

Certain compounds of the invention form pharmaceutically acceptable salts with any of a variety of inorganic and organic bases. Suitable bases for purposes of the invention, are those which form pharmaceutically-acceptable salts such as sodium hydroxide, sodium carbonate, sodium bicarbonate, potassium hydroxide, calcium hydroxide, ammonia and amines. The salt forms may be converted back to their respective acid forms by treatment with an acid such as dilute hydrochloric acid. The acid forms and their respective salts differ in certain physical properties such as solubility but they are otherwise equivalent for purposes of the invention.

Certain compounds of the invention form pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic, and the like. The salts are prepared by contacting the free base form with a sufficient amount of the desired acid to produce a salt in the conventional manner. The free base forms may be regenerated by treating the salt form with a base. For example, dilute aqueous base solutions may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention.

The compounds of the invention may exist in unsolvated as well as solvated forms, including hydrated forms. In general, these solvated forms with pharmaceutically acceptable solvents such as water, ethanol and the like are equivalent to the unsolvated forms for purposes of the invention.

Certain compounds of the invention may exist in isomeric forms. The invention contemplates all such isomers both in pure form and in admixture, including racemic mixtures.

The compounds of this invention can be used to treat allergy caused diseases and their preferred use is for treating allergic chronic obstructive lung diseases. Chronic obstructive lung disease as used herein means disease conditions in which the passage of air through the lungs is obstructed or diminished such as is the case in asthma, bronchitis and the like.

The anti-allergy effects of the compounds of this invention may be identified by tests which measure a compound's inhibition of leukotriene $C_4$ induced contraction of lung smooth muscle. The substance leukotriene $C_4$ is a component of slow reacting substance of anaphylaxis (SRS-A). For example, the compound hexanoic acid, 6,6'-[2-pentadecynylidenebis(oxy)]bis- was found to inhibit leukotriene $C_4$ contractions of lung smooth muscle in such a test procedure in vitro at a concentration of $10^{-5}$ Molar. Said compound was also found to inhibit leukotriene $C_4$ induced bronchospasm in guinea pigs in vivo at an intratracheal dose of 0.5 mg/kg or intravenous dose of 10 mg/kg.

Measurement of Inhibition of Leukotriene $C_4$ Contractions in Vitro

A guinea pig is killed and the lung is removed. The trachea, bronchi and large blood vessals are removed and discarded. Strips of lung parenchyma are prepared from the lower lobes of the lung. The strips are suspended in a heated organ bath containing 10 ml of oxygenated Tyrodes solution. Isometric tension is measured. A contractile response to $10^{-8}$ Molar leukotriene $C_4$ is generated in the absence and presence of test compound and the percent inhibition produced by the test compound is calculated.

Measurement of Inhibition of Leukotriene $C_4$ Bronchospasm in Guinea Pigs in Vivo Fasted male guinea pigs are anesthetized with dialurethane and prepared for the measurement of intratracheal pressure as modified from H. Konzett and R. Rossler, Nauyn-Schmeidebergs Arch Exp Path Pharmakol 195: 71–74, 1940. A bronchospasm [as measured by the increase in intratracheal pressure] is induced by the intratracheal administration of 0.3 ug of leukotriene $C_4$ delivered in 0.1 ml of isotonic saline solution. Test compound is administered either 10 min [intravenous]

or 5 min [intratracheal] before the administration of leukotriene C$_4$. The bronchospasm to leukotriene C$_4$ is measured and a percent inhibition by the test compound is calculated.

When administered orally the compounds of the invention are active at doses from about 10 to 500 mg/kg of body weight; when administered parenterally, e.g., intravenously, the compounds are active at dosages from about 0.1 to 10 mg/kg body weight; when administered by inhalation (aerosol or nebulizer) the compounds are active at dosages of about 0.1 to 5 mg per puff, one to four puffs may be taken every 4 hours.

The compounds of this invention are also useful for the treatment of inflammation. The anti-inflammatory use of the compounds of the present invention may be demonstrated by the Reversed Passive Arthus Reaction (RPAR) Synovitis technique as set forth below using male Lewis rats (obtained from Charles River Breeding Laboratories) weighing 200–250 grams. The potency of the compounds is determined using indomethacin as the standard. On the basis of the test results, an oral dosage range of about 10 milligrams per kilogram of body weight per day to about 500 milligrams per kilogram of body weight per day in divided doses taken at about 4 hour intervals is recommended.

RPAR Synovitis Technique

A Lewis rat is dosed orally with drug or placebo one hour prior to intravenous administration of 2.28 mg of bovine serum albumin (BSA) in 0.2 cc of pyrogen-free saline followed by the intraarticular injection of 0.54 mg of rabbit anti-BSA antibody in 0.03 cc of pyrogen-free saline into one knee joint. The contralateral knee is injected with 0.03 cc of pyrogen-free saline. All injections are made with the animal under light ether anesthesia. Three hours later the rat is again dosed orally with drug or placebo. All drug doses are split. That is, one-half of the dose is administered before lesion induction and one-half is administered after lesion induction.

The following morning (about 17 hours after lesion induction) the rat is killed and both knee joints are exposed. The subpatellar areolar tissue with attendant synovium is excised and weighed. Differences between the weight of antibody and saline injected knees are considered to represent the inflammatory response for each animal (delta synovial weight). Differences in delta synovial weight between lesion controls and drug-treated rats are evaluated for statistical significance with an analysis of variance. Relative potencies are determined with a linear regression analysis.

For preparing pharmaceutical compositions from the compounds described by this invention, inert, pharmaceutically acceptable carriers can be either solid or liquid. Solid form preparations include powders, tablets, dispersible granules, capsules, cachets and suppositories. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter and the like. The term "perparation" is intended to include the formulation of the active compound with encapsulating material as carrier providing a capsule in which the active component (with or without other carriers) is surrounded by carrier, which is thus in association with it. Similarly, cachets are included. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection. Liquid preparations can also be formulated in solution in aqueous polyethylene glycol solution. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the finely divided active component in water with viscous material, i.e., natural or synthetic gums, resins, methylcellulose, sodium carboxymethylcellulose and other well-known suspending agents.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents and the like. The solvent utilized for preparing the liquid form preparation may be water, isotonic water, ethanol, glycerine, propylene glycol and the like as well as mixtures thereof. Naturally, the solvent utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules and powders in vials or ampoules. The unit dosage form can also be a capsule, cachet or tablet itself or it can be the appropriate number of any of these in packaged form.

The quantity of active compound in a unit dose of preparation may be varied or adjusted from 1 mg to 100 mg according to the particular application and the potency of the active ingredient. The compositions can, if desired, also contain other therapeutic agents.

The dosages may be varied depending upon the requirements of the patient, the severity of the condition being treated and the particular compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

EXAMPLE 1

2-Pentadecynyl Aldehyde Dithioacetal of Cysteine N-Triflouoroacetate Methyl Ester A solution of the 2-pentadecynyl aldehyde (0.3098 g) in dry $CH_2Cl_2$ (5 ml) was treated with cysteine methylester N-triflouroacetate, freshly prepared by zinc reduction of the corresponding disulfide (1 g; required 0.9667 g), followed by trimethylsilyl chloride (0.15 g). The reaction was stirred at room temperature for 1 hour. Evaporation of $CH_2Cl_2$ in vacuo gave a gummy residue which was distributed between $CH_2Cl_2$ and water. The $CH_2Cl_2$ phase was separated, and the aqueous phase extracted once with $CH_2Cl_2$. Combined $CH_2Cl_2$ extracts were dried over $Na_2SO_4$ and evaporated to dryness to provide the crude product which was purified on a coarse silica gel (30 g) column using 20–50% diethyl ether in n-hexane. Yield: 0.6893 g.

EXAMPLE 2

1-Butanol, 4,4'-[2-Pentadecynylidenebis(Oxy)]Bis-, Dibenzoate

A mixture of 2-pentadecynyl aldehyde diethylacetal (5.0 g), butane-1,4-diol monobenzoate (6.5 g) and p-toluenesulfonic acid (0.2 g) in dry benzene was refluxed with azeotropic removal of ethanol. After 3 hours the dark reaction solution was washed with aqueous $NaHCO_3$, water, then brine. The solvent was removed in vacuo to give crude product (11.0 g) as a brownish oil which was used as such in the next reaction.

EXAMPLE 3

1-Butanol, 4,4'-[2-Pentadecynylidenebis(Oxy)]Bis-

The product from Example 2 (4.0 g) was hydrolyzed with 30% KOH in aqueous ethanol (120 ml) by refluxing the reaction mixture for 2 hours. Ethanol was evaporated under vacuum and the residue was washed with water. The product was extracted with diethyl ether, dried over $MgSO_4$, filtered and evaporated to dryness in vacuo to give 1.8 g of the product as a yellowish oil.

EXAMPLE 4

Butanoic Acid, 4,4'-[2-Pentadecynylidenebis(Oxy)]Bis-, Dimethyl Ester

A. The acetal-diol (1 g; from Example 3) was dissolved in dry DMF (20 ml) and treated with pyridinium dichromate (8.2 g). The mixture was stirred at room temperature for 20 hours, diluted with 200 ml water and extracted with approximately 400 ml diethylether in portions. Drying over $Na_2SO_4$ and evaporation of the ether extract gave the crude diacid.

The reaction was repeated with acetal-diol (0.488 g) in 10 ml DMF and 4.1 g pyridinium dichromate. Work-up as above gave the crude diacid.

B. The two reactions from above were combined and treated with diazomethane (from 6.5 g diazald). Excess diazomethane was removed by carefully bubbling nitrogen through the solution. Evaporation of diethylether gave the crude diester which was chromatographed on TLC grade silica gel (50 g) using 5% acetone in n-Hexane as eluent. The pure dimethylester (0.6813 g) was obtained as a yellowish oil.

EXAMPLE 5

Butanoic Acid, 4,4'-[2-Pentadecynylidenebis(Oxy)]Bis-

The dimethylester (0.5 g; from Example 4) was dissolved in ethanol (10 ml) and treated with 10% aqueous NaOH (5 ml). After stirring at room temperature for 36 hours, ethanol was evaporated in vacuo, the residue taken up in water and extracted once with diethylether. The remaining aqueous phase was acidified to pH 1.5 with aqueous oxalic acid and extracted with $CH_2Cl_2$. Drying $CH_2Cl_2$ extract over $Na_2SO_4$ followed by evaporation in vacuo provided the pure diacid as a colorless crystalline solid, m.p. 62°–63° C. Yield: 0.4496 g.

EXAMPLE 6

1-Butanol, 4,4'-[2-Nonynylidenebis(Oxy)]Bis-, Dibenzoate

A mixture of 2-nonynyl aldehyde diethylacetal (4.4 g), butane-1,4-diol monobenzoate (8.2 g) and a catalytic amount of p-toluenesulfonic acid in dry benzene was refluxed for 3 hours as in Example 2. Work-up as in Example 2 gave the crude product which was purified by passing through a $SiO_2$ column eluting with hexane and chloroform (1:1) to give 9.0 g of the product.

EXAMPLE 7

1-Butanol, 4,4'-[2-Nonynylidenebis(Oxy)]Bis-

The product from Example 6 (1.0 g) was hydrolyzed with 30% KOH in aqueous ethanol as in Example 3. The product so obtained was purified by preparative TLC using 5% methanol in $CHCl_3$ as eluent. Yield: 0.3 g.

EXAMPLE 8

Butanoic Acid, 4,4'-[2-Nonynylidenebis(Oxy)]Bis-

A. The product from Example 7 (0.5 g) was oxidized with pyridinium dichromate (4.1 g) in 13 ml of dry DMF at room temperature for 2 days. The mixture was diluted with water (350 ml), and extracted with diethylether (3 × 100 ml), washed with water, dried ($Na_2SO_4$) and filtered. The solvent was evaporated to give 0.4 g crude diacid which was methylated with diazomethane followed by chromatography to give pure dimethylester which was hydrolyzed as in Example 5 to give 0.3 g pure diacid.

EXAMPLE 9

Benzene Methanol-4,4'-[2-Pentadecyn-1-Ylidene-Bis(Oxy)Methylene]Bis

The crude reaction mixture containing benzene methanol-4,4'-dibenzoate ester was treated with 100 ml of water, 20 g of KOH and 300 ml of absolute ethanol.

After stirring the mixture at room temperature overnight, it was refluxed for one hour. The solvents were then evaporated, the oily residue was treated with $CH_2Cl_2$, washed with water, and dried over $Na_2SO_4$. After evaporation of the solvent, the mixture was purified via silica gel chromatography (50% EtOAc/Hexanes). Yield: (8.5 g)

EXAMPLE 10

Benzoic Acid-4,4'-[2-Pentadecyn-1-Ylidene Bis(Oxy)Methylene]Bis 1.7 g of benzoic acid-4,4'[2-pentadecyn-1-ylidene bis(oxy)methylene]bis-dimethyl ester were stirred at room temperature in 30 ml of absolute EtOH and 20 ml of 10% aqueous KOH. After two days, the solvents were evaporated under reduced pressure. The residue was taken in water and acidified with aqueous oxalic acid. The precipitate obtained was filtered, washed with water and dried. Yield: 1.6 g.

EXAMPLE 11

A.
Methyl-[4-(Oxy)-Methylacetate)]-3-Oxaoctadec-5-Yn-1-Oate

B.
Methyl-[4-(2-Oxyethanol)]-3-Oxaoctadec-5-Yn-1-Oate 2.0 g of 4-(2-oxyethanol)-3-oxaoctadecen-5yn-1-ol (example 31) in 30 ml dry DMF was added in portions to a solution of pyridinium dichromate (PDC) in 70 ml of dry DMF. After stirring at room temperature for two days, the mixture was poured into water (500 ml). The aqueous solution was extracted several times with $Et_2O$. The combined extracts were washed with water and dried over $Na_2SO_4$. The crude acid resulting from the evaporation of the solvent was treated in $Et_2O$ at 0° C. with large excess of diazomethane solution in $Et_2O$. The esterified mixture (2.0 g) was purified by chromatography on TLC grade silica gel:
Fractions 23–28 gave compound (A), 0.13 g
Fractions 75–85 gave compound (B), 0.11 g.

EXAMPLE 12

Pentanoic Acid-5,5'-[2-Pentadecyn-1-Ylidene-Bis(Oxy)]Bis-Dimethylester

A dry DMF solution (50 ml) of 1-pentanol-5,5'-[2-pentadecyn-1-ylidene-bis(oxy)]bis (example 14) (3.67 g) was added at room temperature to a solution of pyridinium dichromate in 120 ml of dry DMF. After two days the reaction was worked up as in Example 11. The crude reaction mixture was treated at 0° C. in $Et_2O$ with large excess of $CH_2N_2$. The excess diezomethane was destroyed with glacial acetic acid and the reaction mixture was purified by silica gel chromatography (10% EtOAc/Hexanes). Yield: 0.9 g.

EXAMPLE 13

Pentanoic Acid-5,5'-[2-Pentadecyn-1-Ylidene Bis(Oxy)]Bis 0.7 g of pentanoic acid-5,5'-[2-pentadecyn-2-ylidene bis(oxy)]bis-dimethyl ester (example 12) was stirred at room temperature for 24 hours with 10 ml of absolute EtOH and 10 ml of 10% aqueous KOH. The solvents were then evaporated under reduced pressure. The residue was taken in water, acidified with aqueous oxalic acid, and extracted several times with $CH_2Cl_2$. The combined extracts were washed with water and dried over $Na_2SO_4$. Evaporation of the solvent yielded 0.65 g. of the title compound.

EXAMPLE 14

1-Pentanol-5,5'-[2-Pentadecyn-1-Ylidene-Bis(Oxy)]Bis

The crude reaction mixture containing 1-pentanol-5,5'-[2-pentadecyn-1-ylidene bis(oxy)]bis-dibenzoate ester was stirred overnight with 150 ml of water and 300 ml of absolute EtOH containing 25 g of KOH. After refluxing for three hours, the solvents were evaporated under reduced pressure. The residue was treated with $CH_2Cl_2$, washed with water and dried over $Na_2SO_4$. The reaction mixture was purified by silica gel chromatography (50% EtOAc/Hexanes). Yield: 4.0 g.

EXAMPLE 15

Hexanoic Acid, 6,6'-[2-Pentadecynylidenebis(Oxy)]Bis- 3.5 g of 1-hexanol, 6,6'-[2-pentadecynylidenebis(oxy)]bis-in 20 ml of dry DMF was added in portions to a solution of pyridinium dichromate in 70 ml of dry DMF at room temperature. After 24 hours, the reaction was worked up as Example 11. The reaction mixture was purified by silica gel chromatography (first $CHCl_3$; then 5% $MeOH/CHCl_3$). Yield: 70 mg.

EXAMPLE 16

1-Hexanol-6,6'-[2-Pentadecyn-1-Ylidene Bis(Oxy)]Bis

The title compound was prepared and purified in similar manner as in Example 14. The starting material was a mixture containing 1-hexanol-6,6'-[2-pentadecyn-1-ylidene bis(oxy)]bis dibenzoate ester.

EXAMPLE 17

(±)-1-Benzoyloxy-6-(4-Oxybutane-1-Ol)-5-Oxaeicos-7-Yne 3.5 g of benzoyl chloride in 27 ml of $CH_2Cl_2$ was added dropwise, over a period of three hours, at 0° C. to a solution of 1-butanol-4,4'-[2-pentadecyn-1-ylidene bis(oxy)]bis (8.0 g) and dry pyridine (15 ml) in 60 ml of $CH_2Cl_2$. After the addition, the mixture was allowed to warm to room temperature and stirred overnight. The mixture was then diluted with $CH_2Cl_2$ (400 ml), washed with water, and dried over $Na_2SO_4$. After evaporation of the solvent, the reaction mixture (10 g) was purified by silica gel chromatography (10% Acetone/$CHCl_3$). This material was chromatographed again using $CHCl_3$ as eluent. Yield 4.2 g.

EXAMPLE 18

(±)-6-(4-Oxybutan-1-Ol)-5-Oxaeicos-7-Yn-1-Oic Acid 2.2 g of product from Example 17 was oxidized and purified as in Example 15 (eluent: first $CHCl_3$, then 1% $MeOH/CHCl_3$). The product of the oxidation (1.1 g) was hydrolysed and the reaction was worked up as in Example 14. The reaction product was purified by column chromatography ($SiO_2$; eluent: first $CHCl_3$; then 50% $CH_3CN)/CHCl_3$; then 30% $MeOH/CHCl_3$). The product obtained from the elution with 30% $MeOH/CHCl_3$ was purified again ($SiO_2$; 5% $MeOH/CHCl_3$) using the same technique. Yield: 0.16 g.

EXAMPLE 19

6-(4-Oxy-Methylbutanoate)-5-Oxa-Methyl Eicosanoate 1.7 g of butanoic acid-4,4'-[2-pentadecyn-1-ylidene bis(oxy)]bis-dimethylester was dissolved in olefin free petroleum ether (60 ml) and hydrogenated in the presence of 10% Pd/C (0.7 g). After absorption of $H_2$ was complete (3 hours), the catalyst was filtered through celite and washed with $CH_2Cl_2$. The reaction product (1.6 g) obtained after evaporation of the combined filtrates was purified by silica gel chromatography (1% acetone in $CHCl_3$). Yield: 0.8 g.

EXAMPLE 20

Butanoic Acid, 4,4'-[Pentadecylidenebis(Oxy)]Bis- 0.65 g of the product from example 19 was hydrolyzed in 12 ml of absolute EtOH and 8.1 ml of 10% aqueous KOH as in example 13 to provide the pure diacid.

EXAMPLE 21

(±)-1-Benzoyloxy-6-Ethoxy-5-Oxaeicos-7-Yne 32 g of ethane-2,2'-[2-pentadecyn-1-ylidene bis(oxy)]-bis, 25 g of 4-benzoyloxy-1-butanol, and 100 mg of p-toluene sulfonic acid were refluxed in a dry apparatus in 300 ml of benzene using a Dean-Stark trap. After evaporating 75 ml of solvent, the solution was cooled to room temperature diluted with $CHCl_3$, washed with saturated aqueous $NaHCO_3$, then with water and dried over $Na_2SO_4$. The resulting oil (13 g) after evaporation of the solvent was purified by column chromatography ($SiO_2$) ($CHCl_3$). The partially purified compound was rechromatographed ($SiO_2$) (50% Hexanes/$CHCl_3$). Yield: 1.5 g.

EXAMPLE 22

(±)-6-Ethoxy-5-Oxaeicos-7-Yn-1-Ol (±)-1-Benzoyloxy-6-Ethoxy-5-oxaeicos-7-yne was hydrolyzed using the same procedure as described for example 14. The reaction mixture was purified in the same manner using $CHCl_3$ as eluent.

EXAMPLE 23

(±)-6-Ethoxy-5-Oxaeicos-7-Yn-1-Oic Acid 1.2 g of the product from example 22 in 15 ml of dry DMF was added in portions to a solution of pyridinium dichromate (4.4 g) in 30 ml of dry DMF. The solution was stirred at room temperature for 24 hours, then poured into water (300 ml). The aqueous mixture was extracted several times with $Et_2O$, the combined extracts were washed with water and dried over $Na_2SO_4$. The reaction mixture was purified by column chromatography ($SiO_2$) (1% MeOH/$CHCl_3$). The partially purified product (0.54 g) was further purified by preparative thin layer chromatography ($SiO_2$) (2%MeOH/$CHCl_3$). Yield: 0.35 g.

EXAMPLE 24

1-Pentanol, 4,4'-[2-Pentadecynylidenebis(Oxy)]Bis-

The crude mixture containing 1-pentanol, 4,4'-[2-pentdecynylidenebis(oxy)]bis-, dibenzoate ester was hydrolyzed and purified using the same procedure as described for example 14 to provide the title compound.

EXAMPLE 25

Pentanoic Acid, 4,4'-[2-Pentadecynylidenebis(Oxy)]-Bis- 2.6 g of pentanoic acid, 4,4'-[2-pentadecynylidenebis(oxy)]bis-, dimethyl ester was hydrolyzed using the same procedure as described in example 13. Yield: 2.4 g.

EXAMPLE 26

5-Methyl-7-(5-Oxyhexanol)-6-Oxaheneicos-8-Yn-1-Ol

The mixture containing 5-Methyl-7-(5-oxyhexanol)-6-oxaheneicos-8-yn-1-ol-dibenzoate ester was hydrolyzed and purified using the same procedure as described in example 14.

EXAMPLE 27

Hexanoic Acid, 5,5'-[2-Pentadecynylidenebis(Oxy)]Bis-, Dimethyl Ester

The product from example 24 was oxidized, methylated and purified as described in example 12.

EXAMPLE 28

Hexanoic Acid, 5,5'-[2-Pentadecynylidenebis(Oxy)]Bis-

The product from example 27 was hydrolyzed using the same procedure as described for example 13.

EXAMPLE 29

Cis-Methyl-6-(4-Oxy-Methylbutanoate)-5-Oxaeicos-7-En-1-Oate 0.4 g of Lindlar catalyst in petroleum ether (10 ml; olefin and sulfur free) was equilibrated under $H_2$ at room temperature and atmospheric pressure (containing 5 drops of a 5% solution of quinoline in petroleum ether). After four hours, 1.0 g of butanoic acid-4,4'-[2-pentadecyn-1-ylidene bis(oxy)]bis-dimethyl ester in 20 ml of petroleum ether (olefin and sulfur free) was added. The mixture absorbed 47 ml of $H_2$ (theory: 55 ml). The catalyst was then removed by filtration through "Celite" and washed several times with petroleum ether. Evaporation of the solvent yielded 0.9 g of the title compound.

EXAMPLE 30

Potassium-6-(4-Oxy-Potassium Butanoate-5-Oxaeicos-7-En-1-Oate 0.6 g of product from example 29 was dissolved in 15 ml of absolute EtOH and 8 ml of 10% aqueous KOH was added. After stirring at room temperature for 24 hours, the solvents were evaporated and the residue was applied as water solution to 65 g of XAD-4 resin column. The column was eluted first with water, then with MeOH. The fractions containing the compound were combined and treated twice with 30% $Et_2O$/Hexanes. The solvents were decanted and the remaining product dried in vacuo to provide the title compound.

EXAMPLE 31

Ethanol, 2,2'-[2-Pentadecynylidenebis(Oxy)]Bis-

The reaction mixture containing ethanol, 2,2'-[pentadecynylidenebis(oxy)]bis-, dibenzoate ester was hydrolyzed and purified using the same procedure as described in example 14.

EXAMPLE 32

Acetic Acid, 2,2'-[2-Pentadecynylidenebis(Oxy)]Bis- 0.13 g of acetic acid, 2,2'-[2-pentadecynylidenebis(oxy)]bis-, dimethyl ester (Example 11) was hydrolyzed using the same procedure described in example 13. Yield: 0.13 g.

EXAMPLE 33

Butanoic Acid,
4-[[1-[[3-Methoxy-3-Oxo-2(S)-[(Trifluoroacetyl)Amino]Propyl]Thio]-2-Nonynyl]Oxy]-, Methyl Ester A solution of the acetal-dimethylester (0.6627 g from example 8-A) in dry $CH_2Cl_2$ (5 ml) was treated with freshly prepared cysteine methylester N-triflouroacetamide (from 0.4300 g corresponding disulfide) and the mixture cooled (dry ice/cyclohexanone bath). With stirring and in an atmosphere of $N_2$, $BF_3.Et_2O$ (0.05 ml) was syringed in. After 1 hour the reaction flask was allowed to stir outside the cooling bath for ~3 minutes and then quenched with dilute (~7%) $NH_4OH$ solution. Extractive isolation with $CH_2Cl_2$ gave a gummy product (0.9797 g) which was chromatographed on TLC grade silica gel (50 g) using 10% acetone/n-Hexane as eluent. Fractions (5 ml each):
41–51 Pure less polar isomer (0.1287 g)
61–81 Pure more polar isomer (0.0831 g)
Both isomers were obtained as thick oils.

EXAMPLE 34

Butanoic Acid,
4-[[1-[[3-Methoxy-3-Oxo-2(S)-[(Trifluoroacetyl)Amino]Propyl]Thio]-2-Pentadecynyl]Oxy]-, Methyl Ester A stirred solution of the acetal-diester (1 g; from example 4) dissolved in dry $CH_2Cl_2$ (6 ml) was treated with cysteine methylester N-triflouroacetamide (freshly prepared from 0.53 g corresponding disulfide). The mixture was cooled (cyclohexanone/dry ice bath) and the reaction flask was taken out of the cooling bath and let stir for 3–4 minutes followed by treatment with dilute (~7%) $NH_4OH$. Extractive isolation with $CH_2Cl_2$ gave a gummy product (1.4618 g) which was chromatographed on TLC grade silica gel (75 g) using 10% acetone/n-Hexane as eluent. Fractions (5 ml each):
50–58 Pure less polar isomer (0.3783 g)
64–78 Pure more polar isomer (0.2626 g)
Both isomers were obtained as thick oils.

EXAMPLE 35

Butanoic Acid,
4-[[1-[(2(S)-Amino-2-Carboxyethyl)Thio]-2-Pentadecynyl]Oxy]-, Dipotassium Salt (From Less Polar Diastereoisomer)

The dimethylester (0.3783 g; from example 34, less polar isomer) was subjected to hydrolysis with 0.13 M $K_2CO_3$ (100 ml) in MeOH:water (3:1) at room temperature. After ~36 hours solvents were removed in vacuo and the crude dipotassium salt so obtained purified on XAD-4 (140 g) column:
Fraction 1, 600 ml—water (discarded)
Fractions 2–5, 400 ml each—methanol
Evaporation in vacuo provided the product as a amorphous solid, 0.1043 g.

EXAMPLE 36

Butanoic Acid,
4-[[1-[(2(S)-Amino-2-Carboxyethyl)Thio]-2-Pentadecynyl]Oxy]-, Dipotassium Salt (From More Polar Diastereoisomer)

The dimethylester (0.3426 g; from example 34, more polar isomer) was subjected to hydrolysis with 0.13 M $K_2CO_3$ (100 ml) in MeOH:water (3:1) as in example 35. Work-up and purification on XAD-4 column (140 g) provided in fractions 2–5 (400 ml each, MeOH) the product (0.1049 g) as a amorphous solid.

EXAMPLE 37

Butanoic Acid,
4,4'-[4E,6Z,9Z-Pentadecatrien-2-Ynylidenebis(Thio)]-Bis-

A solution of the product from preparative example IV (1.0 g) and 4-mercaptobutanoic acid (1.1 g) in 24 ml of dry $CH_2Cl_2$ was cooled to $-22°$ C. ($CCl_4/CO_2$) (under $N_2$). To this was added $BF_3 Et_2O$ (0.5 ml). The reaction mixture was stirred at this temperature for 2 hours. The mixture was diluted with $CH_2Cl_2$ and washed with water. The organic phase was dried ($Na_2SO_4$) and concentrated to provide the crude product which was purified by passing through 65 g of coarse $SiO_2$ column, using $CHCl_3$:MeOH:AcOH (990:9:1) as eluent to yield 0.98 g of product.

EXAMPLE 38

Hexanoic Acid,
6,6'-[2-Pentadecynylidenebis(Thio)]Bis-

The product from preparative example II (2.0 g) in $CH_2Cl_2$ (15 ml) was treated with 1-mercapto-5-carbomethoxy-pentane (3.9 g) under $N_2$ at room temperature. To this was added $Me_3 SiCl$ (1.5 ml) and the reaction was allowed to stir at room temperature for ½ hour. The solvent was removed under vacuum and the residue was purified on a $SiO_2$ column with gradient elution (hexane; 2% $Et_2O$/hexane; 5% $Et_2O$/Hexane; 10% $Et_2O$/Hexane) to give 3.2 g of product.

EXAMPLE 39

Butanoic Acid, 4,4'-[2-Pentadecynylidenebis(Thio)]Bis-

The product from preparative example II (1.58 g) and γ-mercaptobutyric acid (2.3 g) in 10 ml of dry $CH_2Cl_2$ was treated with $Me_3SiCl$ (1.0 ml) as in Example 38 to afford 1.35 g of product.

EXAMPLE 40

1-Propynl-3,3'-[2-Pentadecyn-1-Ylidene-Bis(Oxy)]Bis 5.0 g of 2-pentadecynal diethyl acetal (preparative example I), 13 ml of propargylic alcohol, and 0.2 g of p-toluene sulfonic acid were refluxed in 200 ml of benzene using a Dean-Stark trap provided with an adapter filled with Dririte. After distilling 170 ml of azeotrope, the residue is diluted with hexanes (200 ml). The organic phase was washed first with aqueous $NaHCO_3$, then with water, dried ($Na_2SO_4$) and evaporated in vacuo to provide the crude product. It was purified by column chromatography ($SiO_2$) eluting first with hexanes (1000 ml), then 3% EtOAC/Hexanes. Yield: 2.4 g.

EXAMPLE 41

1-Butanol 4,4'-[(Tridecylidene)Bis(Oxy)]Bis-Benzoate

To a 3 neck, 100 ml reaction vessel were added: catalytic amount of p-toluenesulfonic acid monohydrate (50 mg), 8.54 g of butane 1,4-diol monobenzoate, and 5 g tridecenal, all in a total 25 ml benzene. The reaction mixture was heated to reflux with azeotropic removal of water. After ~2 hours the reaction was cooled, the benzene solution washed with aqueous $K_2CO_3$ followed by distilled water. The organic phase was dried over $Na_2SO_4$ and evaporated to dryness in vacuo. The crude product so obtained was chromatographed on coarse silica gel (500 g) using 5% acetone in n-Hexane as eluent. Fractions 14 and 15 (200 ml each) were evaporated in vacuo to provide pure dibenzoate (4.23 g) as a thick oil.

EXAMPLE 42

1-Butanol, 4,4'-[Tridecylidenebis(Oxy)]Bis-

A solution of the dibenzoate (1 g; from example 41) in ethanol (20 ml) was treated with aqueous 10% NaOH solution. An additional 20 ml ethanol was added to obtain a homogenous solution. After stirring at room temperature for ~48 hours, the reaction was worked up as in example 3 to provide virtually pure product as a yellowish oil. It was used as such in the next reaction.

EXAMPLE 43

1-Butanoic Acid, 4,4'-[(Tridecylidene)Bis(Oxy)]Bis-Dimethyl Ester

The diol (1 g; from example 42) was oxidized with pyridinium dichromate (7.33 g) in dry DMF (14 ml) as in example 4A to provide crude diacid which was treated with diazomethane as in example 4B. Chromatography of the crude dimethylester on TLC grade silica gel (30 g) using 5% acetone in n-Hexane as eluent provided the pure dimethylester (0.28 g) as a yellow oil.

EXAMPLE 44

1-Butanoic Acid, 4,4'-[(Tridecylidene)Bis(Oxy)]Bis

A solution of the dimethylester (0.2 g; from example 43) in ethanol was treated with 10% aqueous NaOH (2 ml) and the mixture refluxed for 4 hours. Work-up of the reaction as in example 5 yielded the pure diacid (0.15 g) as a crystalline solid, m.p. 33° C.

EXAMPLE 45

6-[(3-Carboxypropyl)Thio]-7-Eicosynoic Acid,

A mixture of methyl 6-bromo-7-eicosynoate (3.0 g), methyl 4-mercaptobutanoate (1.0 g), $Cs_2CO_3$ (2.44 g) in DMF (70 ml) was stirred at room temperature for 2 hours. After dilution with water followed by extraction with $Et_2O$ afforded 4.0 g crude product which was purified on $SiO_2$ (200 g) column. Elution with 50% hexane/$CHCl_3$ gave 1.7 g pure eicosanoate.

The diester (1.42 g) from above was hydrolyzed with 10 ml 10% KOH and 20 ml EtOH at room temperature for 5 hours. After work-up as in example 5, the pure diacid was obtained as a solid (1.22 g).

EXAMPLE 46

6-[(5-Carboxypentyl)Thio]-7-Eicosynoic Acid

A mixture of methyl 6-bromo-7-eicosynoate, methyl 6-mercaptohexanoate (1.21 g) in 70 ml DMF was treated with $Cs_2CO_3$ (2.44 g) as in Example 45 to give 1.02 g of methyl-6-[(6-methoxy-6-oxohexyl)thio]-7-eicosynoate.

The diester (0.72 g) from above was hydrolyzed in a similar manner as in Example 45 to give the title compound as a solid (0.53 g).

EXAMPLE 47

6-[(2-Carboxyethyl)Thio]-7-Eicosynoic Acid

To a stirred slurry of 0.58 g of NaH (50%) in $Et_2O$ (12 ml) at 0° C. was added dry $CF_3CH_2OH$ (0.93 ml). After the $H_2$ evolution had ceased, a solution of triphenylphosphine (1.58 g) in 12 ml of $CH_2Cl_2$ was added. After stirring for 10 min, 0.3 ml bromine was added. This mixture was then stirred at 0° C. for 1 hour, followed by addition of a solution of the product from preparative example VI (1.7 g) and methyl-3-mercaptopropionate (0.55 ml) in $CH_2Cl_2$ (2.5 ml). The mixture was stirred at room temperature for 7 hours. The reaction was quenched with water and extractive isolation with $CH_2Cl_2$ yielded 2.5 g crude product. Chromatography on 100 g $SiO_2$ using 30% hexane in $CH_2Cl_2$ as eluent gave 0.66. g of methyl 6-[(3-methoxy-3-oxopropyl)thio]-7-eicosynoate.

The above product (1.3 g) was hydrolyzed with 12.2 ml of 10% NaOH in 25 ml EtOH at room temperature for 17 hours. Work-up as in example 5 yielded 0.91 g of the product as a yellowish solid.

EXAMPLE 48

Potassium 6-[[2-[(Trifluoroacetyl)Amino]Ethyl]Thio]-7-Eicosynoate

The product from example 49 (0.5 g) in 40 ml dry MeOH was treated with 0.5 g of S-ethyl-thiotrifluoroacetate and was stirred at room temperature for 1 hour. The MeOH was removed in vacuo to give 0.57 g the title compound as a yellowish liquid.

EXAMPLE 49

Potassium 6-[(2-Aminoethyl)Thio]-7-Eicosynoate

Methyl 6-[[2-(trifluoroacetyl)ethyl]thio]-7-eicosynoate was prepared in a manner similar to Example 47, except that N-(2-mercaptoethyl)trifluoroacetamide was used instead of methyl 3-mercaptopropanoate.

The above product (1.0 g) was hydrolyzed with 50 ml of 0.13M $K_2CO_3$ in MeOH/$H_2O$ (3:1) at room temperature for 48 hours and subjected to purification on a XAD-4 (250 g) column to yield 0.56 g of product.

EXAMPLE 50

(±) Trans-6-[(2-Amino-2-Carboxyethyl)Thio]-5-Hydroxy-7-Eicosynoic Acid, Dipotassium Salt Hydrolysis of (±)-methyl 5-hydroxy-6-[[3-methoxy-3-oxo-2-](trifluoroacetyl)amino]propyl]thio]-7-eicosynoate (0.23 g) in a manner similar to example 49 provided 0.16 g of the title compound.

EXAMPLE 51

(±)-6-[(2-Amino-3-Methoxy-3-Oxopropyl)Thio]-7-Eicosynoic Acid (The synthesis of the title compound is described in part E of this example.)

Part A

To a solution of dry cyclohexanone (20 g) in dry Et$_3$N (125 ml) in dry DMF (125 ml) was added in one portion 61.2 g of t-butyldimethyl chlorosilane. The mixture was refluxed under N$_2$ for two days. After cooling to room temperature, the mixture was diluted with Et$_2$O, washed with aqueous NaHCO$_3$, then with 0.1N HCl, then again with saturated aqueous NaHCO$_3$, and finally with water, and dried over Na$_2$SO$_2$. The oil, resulting from the distillation of the solvents, was purified by fractional distillation. Yield: 22 g. B.p=70°–73° C./4 mm, Hg.

Part B

A solution of 10 g of the product from part A in 150 ml dry CH$_2$Cl$_2$ and 15 ml t-butanol was ozonized at −78° C. for ½ hour. The excess O$_3$ was kept in solution for 15 more minutes, then bubbled off with N$_2$. (CH$_3$)$_2$S (10 ml) was added at −78° C., then the solution was allowed to warm to room temperature and kept overnight. After evaporation of the solvent, the resulting oil was purified by fractional distillation. After distilling the fraction boiling at 44°–50° C./4 mm Hg, the residue was used as such.

Part C 14.8 ml of a 3.0 molar solution of EtMgBr in Et$_2$O was added at room temperature with stirring under N$_2$ to 10.0 gr of 1-tetradecyne in 20 ml of dry Et$_2$O. After the addition, the solution was stirred for another hour, then added to a precooled solution (dry ice-acetone bath) of the aldehyde prepared as described in part B (10.0 g) in 75 ml of dry Et$_2$O. After the addition, the thick paste formed was allowed to warm to room temperature and stirred for one hour; then 75 ml of saturated aqueous NH$_4$Cl was added in portions. The organic layer was separated, and the aqueous layer extracted several times with Et$_2$O. The combined extracts were washed with water and dried over Na$_2$SO$_4$. The oil resulting from the evaporation of the solvent, was purified by fractional distillation.

The fractions distilling between 80° and 100° C. at 3 mm Hg were discarded. The residue was used as such for part D.

Part D 5.0 g of the product prepared as described in part C was dissolved in 50 ml of dry CH$_2$Cl$_2$ and 10 ml of dry pyridine and the solution cooled (ice bath). A solution of methanesulfonic anhydride (2.85 g) in 20 ml of dry CH$_2$Cl$_2$ was added dropwise. After the addition, the mixture was let warm up and stirred at room temperature for three hours, then diluted with CH$_2$Cl$_2$. The CH$_2$Cl$_2$ solution was washed twice with water, then with aqueous NH$_3$ (1:10), then again with water and dried over Na$_2$SO$_4$. The reaction product (5.4 g) obtained after evaporation of the solvent was used as such for part E.

Part E 2.0 g of the product prepared as described in part D, t-butanol (7 ml), cysteine methyl ester hydrochloride (1.46 g), and 4 ml of dry Et$_3$N were mixed in the order under N$_2$ at room temperature. After 24 hours, 20 ml of dry CH$_2$Cl$_2$ was added and the mixture stirred for another 24 hours. The solvents were then evaporated, and the reaction mixture was purified by column chromatography (silica gel). The column was eluted first with CHCl$_3$ (3 liters), then with 20% MeOH/CHCl$_3$. The combined fractions containing the compound (2.7 g) were chromatographed again on silica gel. The column was eluted successively with CHCl$_3$ (1 liter), 5% MeOH/CHCl$_3$, 10% MeOH/CHCl$_3$, and 20% MeOH/CHCl$_3$. The fractions containing the compound were combined and purified by preparative thin layer chromatography on silica gel [solvent: 10% (MeOH:NH$_3$)/CHCl$_3$ (9:1); two elutions] yield: 0.05 g.

EXAMPLE 52

Cysteine, (±)-(1-Pentyl-2-Pentadecynyl)-N-(Trifluoroacetyl)-, Methyl Ester

Part A

The reaction conditions were the same as in part C of example 51 except that hexanal was used as one of the reactants.

Part B

The reaction conditions were the same as in part D of example 51.

Part C 1.99 g of the product as obtained from part B, tert-butanol (10 ml), 2.97 g of cysteine methyl ester N-trifluoroacetate and dry Et$_3$N (2.5 ml) were racted as described in example 53. The reaction mixture was purified by column chromatography (silica gel) (CHCl$_3$). The fractions containing the product were combined and purified again as above using 50% CHCl$_3$/Hexanes as eluent. The pure fractions were combined to provide the title compound.

EXAMPLE 53

(±)-6-[(2-Amino-3-Methoxy-3-Oxopropyl)Thio]-7-Eicosynoic Acid 1.97 of crude product prepared as described in part D of example 51, tert-butanol (7 ml), N-trifluoroacetyl cysteine methyl ester (2.0 g), and Et$_3$N (2 ml) were added at room temperature. The solution was stirred at room temperature under N$_2$ for four hours. The solvents were then evaporated under reduced pressure and the dark oily residue obtained was treated with water and extracted with CHCl$_3$. The CHCl$_3$ extract was washed with water, dried (Na$_2$SO$_4$) and evaporated to dryness. The reaction product (3.6 g) was purified by column chromatography (silica gel). The column was successively eluted with CHCl$_3$, and 10% MeOH/CHCl$_3$. The fractions containing the title compound were combined and purified again as above. The column was eluted first with CHCl$_3$, then with 2% MeOH/CHCl$_3$. The fractions containing the pure product were combined and evaporated in vacuo to provide the title compound.

EXAMPLE 54

Cysteine, (±)-(1-Pentyl-2-Pentadecynyl)-, Potassium Salt 0.64 g of compound from example 52 was stirred at room temperature under N$_2$ with 60 ml of 0.13M K$_2$CO$_3$ in MeOH:H$_2$O (3:1) for 16 hours. Aqueous KOH (0.35 g/ml water) was added and the reaction stirred for 20 hours at room temperature. The solvents were evaporated under high vacuum. The solid residue was treated with water (25 ml) and the pH of the solution adjusted to 5.2. The mixture was taken in CHCl$_3$ and the aqueous layer was separated. The organic layer was washed with water and dried over Na$_2$SO$_4$. Evaporation of the solvent gave the title compound.

EXAMPLE 55

7-Eicosynoic Acid, (±)-6-[(2-Amino-2-Carboxyethyl)Thio]-, Dipotassium Salt 0.4818 g of product from example 53 was treated with 20 ml MeOH:H$_2$O (3:1) and cooled in ice bath under N$_2$. 0.5 g of KOH in 3 ml of water was then added dropwise. The solution was let warm up to room temperature and stirred for a total of four hours. Aqueous KOH (0.25 g/ml) was added and after another hour, the solvents were evaporated under reduced pressure. The residue was dissolved in water (10 ml) and applied to an XAD-4 column (145 g). The column was successively eluted with water (10×20 ml), 30% MeOH/H$_2$O (6×20 ml), 50% MeOH/H$_2$O (5×20 ml) and MeOH (11×20 ml). The methanolic fractions gave 0.28 g of the title compound.

EXAMPLE 56

(±)-6-[[2-Carboxy-2-[(Trifluoroacetyl)Amino]Ethyl]-Thio]-7-Eicosynoic Acid 0.4 g of compound prepared according to example 53 was stirred at room temperature under N$_2$ in 57 ml of 0.13M K$_2$CO$_3$ in MeOH:H$_2$O (3:1) for five hours. The solvents were evaporated under high vacuum and the residue was purified using 250 g XAD-4 resin column in water. The column was eluted with water to pH=7, then with 250 ml of 30% MeOH/H$_2$O, 500 ml of 50% MeOH/H$_2$O, and 100% MeOH. The product (0.16 g) was further purified by preparative thin layer chromatography on SiO$_2$ (40% MeOH/CHCl$_3$). Yield: 0.035 g.

EXAMPLE 57

(±)-6-[[3-Methoxy-3-Oxo-2-[(Trifluoroacetyl)Amino]-Propyl]Thio]-7-Eicosynoic Acid, Methyl Ester 0.7 g of the product prepared according to example 53 was treated at 0° C. in Et$_2$O with large excess of CH$_2$N$_2$ in Et$_2$O. Solvent was evaporated under N$_2$ at room temperature. The reaction mixture was purified by column chromatography (SiO$_2$) (CHCl$_3$). Yield: 0.22 g.

EXAMPLE 58

2H-Pyran, Tetrahydro-2-[[6-[[6-[(Tetrahydro-2H(±)-Pyran-2-Yl)Oxy]-Hexyl]Oxy]-7-Eicosynyl]Oxy- Part A 21 ml (2.85M in Et$_2$O) EtMgBr was added dropwise to a solution of 1-tetradecyne in 120 ml of dry Et$_2$O at room temperature. After the addition, the brown solution was stirred at room temperature for one hour, then cooled (dry ice-acetone bath). 10.0 g 6-[(tetrahydro-2H-pyran-2-yl)oxy]-hexanal in 50 ml of dry Et$_2$O was added in one portion. The mixture was let warm up to room temperature and stirred for two hours. 3.5 g NH$_4$Cl in 30 ml water was then added. The mixture was diluted with Et$_2$O (total volume=750 ml), washed with water, and dried over Na$_2$SO$_4$. The reaction mixture resulting from the evaporation of the solvent (20 g) was filtered through silica gel (350 g) using CHCl$_3$ as eluent. The product obtained (3.6 g) was used as such for part B.

Part B 0.9 g NaH (50% oil dispension) was washed with hexanes under N$_2$, then 4 ml of dry THF was added. 2.66 g of the product from part A was added at room temperature, and the mixture refluxed under N$_2$ for three hours. After cooling to room temperature, 3.0 g of 1-iodo-6-tetrahydropyran-2-yl-ether was added and the mixture refluxed overnight under N$_2$. The mixture was then cooled in ice bath and treated with water. The solution was taken in CH$_2$Cl$_2$ (300 ml), washed with water to pH=7 and dried over Na$_2$SO$_4$. The reaction product was purified by column chromatography (silica gel) (5% EtOAc/Hexanes). Yield: 1.0 g.

EXAMPLE 59

(±)-6-[(6-Hydroxyhexyl)Oxy]-7-Eicosyn-1-Ol 1.0 g of 2H-Pyran, tetrahydro-2-[[6-[[6-[(tetrahydro-2H-pyran-2-yl)oxy]hexyl]oxy]-7-eicosynyl]oxy]- was stirred at room temperature for seven hours with 15 ml methanol containing 50 mg of p-toluenesulfonic acid. The solution was kept overnight in the refrigerator, then treated with 3 ml MeOH:aq. NH$_3$ (8:2). After evaporation of the solvents, the resulting oil was taken in CH$_2$Cl$_2$ washed with water (3×50 ml), and dried over Na$_2$SO$_4$. Yield: 0.65 g.

EXAMPLE 60

(±)-6-[(6-Methoxy-6-Oxohexyl)Oxy]-7-Eicosynoic Acid, Methyl Ester

The product from example 59 was oxidized and methylated using the same procedure as described in example 11. The reaction mixture was purified by column chromatography on silica gel (5% EtOAc/Hexanes).

EXAMPLE 61

(±)-6-[(5-Carboxypentyl)Oxy]-7-Eicosynoic Acid

The product from example 60 (0.2 g) was hydrolysed using the same procedure as described in example 13. Yield: 0.195 g.

EXAMPLE 62

(−)-Methyl(5R,6S)-5-Hydroxy-6-[(2R)-2-(Trifluoroacetylamino)-2-(Methoxycarbonyl)-Ethylthio]-7-Eicosynoate and (+)-Methyl(5S,6R)-5-Hydroxy-6-[(2R)-2-(Trifluoroacetylamino)-2-(Methoxycarbonyl)-Ethylthio]-7-Eicosynoate A solution of methyl-trans-5,6-epoxy-7-eicosynoate (0.3762 g) (preparative example X) in methanol (0.1 ml) containing Et$_3$N (0.8 g) was treated After 2 hours solvents were evaporated in vacuo and the residue distributed between water and CH$_2$Cl$_2$. The organic phase was then separated and the aqueous phase extracted three times with CH$_2$Cl$_2$. Combined CH$_2$Cl$_2$ extracts were washed once with water, dried (Na$_2$SO$_4$) and evaporated to dryness in vacuo to provide a thick yellow oil (1.0097 g). The reaction was repeated exactly as above using 1.22 g. trans-epoxide to provide another batch of the product (3.228 g). The two products were combined and chromatographed on TLC grade silica gel using 20–30% ethylacetate in n-Hexane as eluent:
A. Less polar isomer 0.94 g, $[\alpha]_D^{26}$−10.9°(CHCl$_3$).
B. More polar isomer 0.66 g, $[\alpha]_D^{26}$+22.1°(CHCl$_3$).
Both isomers were obtained as waxy solids.

EXAMPLE 63

(−)-(5R,6S)-5-Hydroxy-6-[(2R)-2-Amino-2-Carboxyethylthio]-7-Eicosynoic Acid Dipotassium Salt The less polar dimethylester from example 62 (0.4 g) was stirred with 90 ml 0.13M K$_2$CO$_3$ in MeOH:water (3:1) at room temperature in N$_2$ atmosphere. After 36 hours solvents were removed in vacuo (bath temp. 40° C.) and the residue obtained subjected to purification on a XAD-4 (160 g) column:

Fractions: water (800 ml)—discarded 1–5 MeOH 0.2783 g amorphous solid (400 ml) each [α]$_D^{26}$ −24.6°- (MeOH).

EXAMPLE 64

(+)-(5S,6R)-5-Hydroxy-6-[(2R)-2-Amino-2-Carboxyethylthio]-7-Eicosynoic Acid Dipotassium Salt The more polar dimethylester (0.3 g) was stirred with 66 ml 0.13M K$_2$CO$_3$ in MeOH:water (3.1) at room temperature in N$_2$ atmosphere. After 36 hours the reaction was worked up as in example 63 and the product subjected to purification on a XAD-4 (120 g) column:

Fractions: Water (600 ml) 1–5 MeOH 0.2264 g (400 ml each) amorphous solid [α]$_D^{26}$+11.9°(MeOH).

EXAMPLE 65

6-HYDROXY-6-(1-TETRADECYNYL)-UNDECANEDIOIC ACID (CRUDE)

A stirred solution of 1-tetradecyne (58.2 g) in 55 ml dry tetrahydrofuran (THF) was treated (in argon atmosphere) dropwise with n-BuLi (1.6M in n-Hexane) until 85 ml had been added. A very heavy precipitation of Li-salt of 1-tetradecyne took place causing difficulty in stirring the reaction mixture. After stirring the reaction mixture in ice bath for ∼45 minutes, 6-oxo undecanedioic acid (10.4 g) was added as a concentrated solution in dry THF (50 ml). The reaction mixture was gradually allowed to warm up to room temperature and stirred for a total 15 hours. The pasty reaction mixture was quenched with water and extracted with n-hexane to remove excess 1-tetradecyne. The aqueous phase was adjusted to pH∼2 with aqueous oxalic acid and extracted with CH$_2$Cl$_2$. A crystalline solid not soluble in either phase later found to be unchanged oxo-dicarboxylic acid was removed by filtration. The CH$_2$Cl$_2$ extract was dried (Na$_2$SO$_4$) and evaporated to dryness to provide a crystalline solid. Yield: 6.36 g. This product was used as such in the next reaction.

EXAMPLE 66

UNDECANEDIOIC ACID, 6-HYDROXY-6-(1-TETRADECYNYL)-, DIMETHYLESTER

The crude diacid from example 65 (0.6 g) was treated with excess diazomethane as in example 4B and subjected to chromatography on six 1 mm thick silica gel plates (solvent system: 20% ethylacetate in n-hexane). The less polar major band was extracted with 20% MeOH/CHCl$_3$ to provide a crystalline solid, m.p. 35° C. Yield: 0.44 g.

EXAMPLE 67

6-HYDROXY-6-(1-TETRADECYNYL)UNDECANEDIOIC ACID (PURE)

A solution of the pure diester from example 66 (0.22 g) in ethanol (5 ml) was treated with 10% aqueous NaOH (2.5 ml). The mixture was stirred for 36 hours at room temperature. Work-up of the reaction as in example 5 yielded a crystalline solid, m.p. 65°–66° C. Yield: 0.191 g.

EXAMPLE 68

6-(1-TETRADECYNYL)UNDEC-5Z-ENEDIOIC ACID, DIMETHYLESTER

A solution of the tert. alcohol-dimethylester from example 66 (1 g) in CH$_2$Cl$_2$ (50 ml) was treated with cooling (bath temp 0°–5° C.) and good stirring with P$_2$O$_5$ (0.8 g). After 1 hour the reaction was quenched with water. CH$_2$Cl$_2$ phase was separated and the aqueous phase was extracted twice with more CH$_2$Cl$_2$. The combined CH$_2$Cl$_2$ extract was washed with aqueous NaHCO$_3$, dried over Na$_2$SO$_4$ and evaporated to dryness to provide the crude product (1.035 g) as a thick oil. It was purified by chromatography on coarse SiO$_2$ (30 g) using 10% ethylacetate in n-hexane as eluent (50 ml fractions). The desired 5Z-olefin was obtained as the less polar component. Yield: 0.7564 g. The more polar fraction was a mixture of 5Z-(major) and 5E-(minor) olefins (0.2028 g).

EXAMPLE 69

6-(1-TETRADECYNYL)UNDEC-5Z-ENEDIOIC ACID

A solution of the dimethylester from example 68 (0.2 g) in ethanol (5 ml) was treated with 10% aqueous NaOH (2.5 ml). The reaction mixture was stirred for 36 hours and worked up as in example 5 to provide the title compound as a crystalline solid, m.p. 47°–48° C. Yield: 0.196 g.

EXAMPLE 70

6-(1-TETRADECYNYL)-UNDEC-5E-ENEDIOIC ACID, DIMETHYLESTER

Dedhydration of 7 g. tert. alcohol-dimethylester (from example 66) was conducted as in example 68. The minor more polar 5E-olefin was isolated by repeated chromatography on TLC grade silica gel using 10% ethylacetate in-hexane as eluent. The partially purified 5E-olefin (0.149 g) was further purified by preparative thin layer chromatography.

EXAMPLE 71

6-(1-TETRADECYNYL)UNDEC-5E-ENEDIOIC ACID

Hydrolysis of the 5E-olefin-dimethylester (0.16 g) as in example 69 gave the title compound as a crystalline solid. Yield: 0.15 g.

EXAMPLE 72

UNDECANEDIOIC ACID, 6-FLUORO-6-(1-TETRADECYNYL)-, DIMETHYLESTER

A stirred solution of the 6-hydroxy-dimethylester (1 g; example 66) in CH$_2$Cl$_2$ (5 ml) was cooled (ice bath) and treated with diethylaminosulfurtrifluoride (DAST) (0.7 ml; excess). After 30 minutes in the ice bath, the reaction was allowed to warm up to room temperature. The reaction mixture was stirred for a total of 1½ hours followed by treatment with dilute NaHCO$_3$ solution. CH$_2$Cl$_2$ layer was separated and the aqueous phase extracted once more with CH$_2$Cl$_2$. The combined organic extracts were washed once with water, dried (Na$_2$SO$_4$) and evaporated to dryness to provide a gummy product. It was chromatographed on TLC grade SiO$_2$ (50 g) using 10% ethylacetate in n-hexane as eluent (∼5 ml fractions). The desired 6-fluoro-dimethylester was isolated from the more polar fractions 47–52 as a colorless oil. Yield: 0.4856 g.

EXAMPLE 73

6-FLUORO-6-(TETRADECYNYL)UNDECANEDIOIC ACID

A solution of the fluoro-diester from example 72 (0.22 g) in ethanol was hydrolysed with 10% aqueous NaOH (3 ml) as in example 5. Work-up in the same manner provided the desired diacid as a crystalline solid, m.p. 98°–100° C. Yield: 0.2051 g.

EXAMPLE 74

6-FLUORO-6-TETRADECYLUNDECANEDIOIC ACID, DIMETHYLESTER

A solution of the acetylenic product (0.4 g); from example 73) in n-hexane (40 ml) was hydrogenated in the presence of 10% Pd/C (0.1 g). After 15 hours the catalyst was removed by filtration, washed with $CH_2Cl_2$ and the combined filtrates and washings were evaporated to dryness to provide a thick colorless oil. Yield: 0.4 g.

EXAMPLE 75

6-TETRADECYLUNDECANEDIOIC ACID, DIMETHYLESTER

A solution of the unsaturated diester (0.3 g; example 68) in n-hexane (30 ml) was hydrogenated in the presence of 10% Pd/C (0.1 g) overnight. Catalyst was removed by filtration and washed with $CH_2Cl_2$. Evaporation of combined filtrates gave the title compound as a thick colorless oil. Yield: 0.3 g.

EXAMPLE 76

6-TETRADEUNDECANEDIOIC ACID

A solution of the diester (0.2 g; from example 75) in ethanol (5 ml) was treated with 10% aqueous NaOH (2.5 ml) exactly as in example 5 to provide a crystalline solid, m.p. 48°–50° C.

EXAMPLE 77

6-HYDROXY-6-TETRADECYLUNDECANEDIOIC ACID

A solution of the saturated diester (0.23 g; example 74) in ethanol (8 ml) was treated with 10% aqueous NaOH (2.5 ml) as in the previous experiment. The product after trituration with n-hexane provided a crystalline solid, m.p. 79°–80° C. Yield: 0.1896 g.

EXAMPLE 78

6-(51-TETRADECYNYL-UNDECANEDIOIC ACID (The synthesis of the title compound is described in part E of this example)

Part A

To a solution of 6-(1-tetradecynyl)undec-5Z-enedioic acid dimethylester (1.0 g.; example 68) was added (under $N_2$) dicobalt octacarbonyl (0.94 g.) in dry $CH_2Cl_2$ at room temperature. The reaction was stirred for 1 hr. followed by removal of $CH_2Cl_2$ under $N_2$ atmosphere.

Part B

A solution of the product from the above reaction (1.5 g.) in dry methanol (25 ml) was added to a slurry of potassium diazodicarboxylate (5.06 g.) in dry methanol (25 ml) in an atmosphere of $N_2$. The reaction mixture was cooled (ice bath) and a solution of glacial acetic acid (2.7 ml) in dry methanol (7.3 ml) was added dropwise. The mixture was stirred in ice bath for three hours. Four additions of potassium diazodicarboxylate (as a solid) (3.3 g.) along with glacial acetic acid (1.5 ml) in dry methanol (8.5 ml) were necessary at three hour intervals. After evaporation of methanol in vacuo the residue was dissolved in $CHCl_3$, washed with aqueous $NaHCO_3$, water and dried ($Na_2SO_4$). Evaporation of the solvent in vacuo left the crude product (1.07 g.).

Part C

A portion of the reaction product from above (0.722 g.) was dissolved in acetone (25 ml) and the solution cooled (ice bath). Ceric ammonium nitrate (3.3 g.) was added in small portions over a period of 30 minutes with good stirring. The reaction mixture was stirred for an additional 15 minutes followed by addition of n-hexane (200 ml). the organic phase was washed with water, dried ($Na_2SO_4$) and evaporated to dryness to provide the crude dimethylester of the title compound containing unchanged olefinic dimethylester.

Part D

The above mixture was treated with m-chloroperbenzoic acid as described in preparative example XII. A mixture of the epoxide derived from the unchanged olefinic dimethylester and unreacted dimethylester of the title compound was thus obtained. The two products were separated by chromatography on t.l.c. grade silica gel. The pure dimethylester of the title compound so obtained was treated as follows.

Part E

A portion (0.1 g.) of 6(1-tetradecynyl)undecanedioic acid dimethylester (as obtained from Part D) was treated with 10% aqueous KOH as in example 13 to provide the title compound. Yield: 0.09 g.

EXAMPLE 79

HEPTANOIC ACID-6,6'-[PENTADECYN-1-YLIDENE BIS(OXY)]-BIS-(2,2-DIMETHYL-1-OXOPROPOXYMETHYL)ESTER

To a stirred solution of heptanoic acid-6,6'-[2-pentadecyn-1-ylidene bis(oxy)]bis (0.5 g) in dry DMF (3 ml) was added dry $Et_3N$ (0.77 ml). The solution was cooled in an ice bath and a solution of chloromethyl pivalate (0.34 ml) was added. The solution was allowed to warm to room temperature and stirred in an argon atmosphere for ~15 hrs. The solvent was evaporated in vacuo, the residue treated with water (20 ml) and extracted several times with ethyl acetate. The combined extracts were washed with water, dried ($Na_2SO_4$) and evaporated to dryness to provide a gummy product. The impure product was filtered through a column of $SiO_2$ (30 g) using $CHCl_3$ as eluent. Yield: 0.7 g.

PREPARATIVE EXAMPLE I

2-PENTADECYNAL DIETHYLACETAL

1-Tetradecyne (100 g), $(EtO)_3CH$ (200 ml) and $ZnI_2$ (15 g) were heated together (bath temperature 170°–175°) with distillative removal of ethanol (~90 minutes). The reaction mixture was evaporated in vacuo (bath temperature 80°) to remove excess $(EtO)_3CH$. The residue was distributed between $CH_2Cl_2$ and water. The $CH_2Cl_2$ phase was separated, washed with aqueous $NaHCO_3$, dried ($Na_2SO_4$) and evaporated in vacuo to provide a light brown oil. Yield:

135.4 g. This product was shown to be virtually pure by TLC and PMR and it was used as such in subsequent reactions.

PREPARATIVE EXAMPLE II

2-PENTADECYNAL

A mixture of 2-pentadecynal diethyl acetal (4 g) and 10% aqueous $H_2SO_4$ (60 ml) was refluxed with efficient stirring, for one hour. An additional 40 ml dilute $H_2SO_4$ was added at this stage and the mixture heated for another two hours. After cooling, the reaction mixture was extracted with $CH_2Cl_2$, the extract dried ($Na_2SO_4$) and evaporated in vacuo to provide a yellow oil. Yield: 2.9 g.

PREPARATIVE EXAMPLE III

2E-HEXEN-4-YNAL, 6,6-DIETHOXY-

A stirred solution of diformyl acetylene monodiethylacetal (2.28 g) was treated in small portions with $Ph_3P=CH.CHO$ (4.47 g). After stirring for 15 hours the solvent was evaporated in vacuo and the dark residue subjected to chromatography on coarse $SiO_2$ (100 g) using 5% acetone/n-hexane as eluent. Fractions (100 ml) were collected and the title compound was obtained pure from fraction no. 6. Yield: 2.01 g.

PREPARATIVE EXAMPLE IV

4E,6Z,9Z-PENTADECATRIENE-2-YNE ALDEHYDE DIETHYL ACETAL

A solution of 3-(Z)-nonene-triphenylphosphonium salt in 20-23 ml of dry THF was treated with 1.6M BuLi (6.79 ml) and stirred at room temperature for 1 hour. The aldehyde (1.68 g, example III) in 3 ml THF was added and allowed to stir for another 3 hours. The reaction mixture was diluted with EtOAc and washed with dilute $NaHSO_3$ solution, brine and dried ($Na_2SO_4$). Evaporation of the solvent followed by chromatography on $SiO_2$ (eluent 10% $Et_2O$ in n-hexane) gave the pure product (1.17 g) as a yellow oil.

PREPARATIVE EXAMPLE V

(±) METHYL-6-HYDROXY-7-EICOSYNDOATE

A cooled solution (ice bath) of the 6-ketone (29.86 g) in methanol (475 ml) and water (10 ml) was treated with $NaBH_4$ (1.27 g) in small portions. After 30 minutes the reaction was diluted with water (50 ml), methanol evaporated in vacuo and the residue distributed between water (50 ml) and $CH_2Cl_2$ (100 ml). $CH_2Cl_2$ phase was extracted twice with $CH_2Cl_2$. The combined $CH_2Cl_2$ extracts were dried ($Na_2SO_4$) and evaporated to dryness to provide the almost pure alcohol as a thick oil (30.23 g). It was further purified on coarse silica gel (300 g) using 5% ethyl acetate/n-hexane as eluent. Fractions 7-18 (250 ml each) gave the pure alcohol. Yield: 21.79 g.

PREPARATIVE EXAMPLE VI

(+) METHYL 6(R)-HYDROXY-7-EICOSYNOATE

A solution of (+) α-pinene (1.04 ml; $[\alpha]_D^{26} + 47.7°$) and 9-borabicyclononane (12 ml of 0.5M THF solution; 0.006 mol) was refluxed for 2½ hours and cooled to room temperature. With ice bath cooling methyl 6-oxo-7-eicosynoate (1 g; 0.003 mol) was now added. The mixture was now stirred under argon at room temperature for 3 days. Acetaldehyde (21 ml) was injected into the solution which was then stirred for 15 minutes. The THF and (+) α-pinene were removed in vacuo at 40° (bath temperature). The remaining yellow product was treated with diethylether (5 ml) to dissolve, followed by addition of ethanolamine (0.38 g; 0.006 mol). After stirring at ice bath temperature for 15 minutes the white precipitate formed was removed by filtration and washed with cold diethylether. The combined filtrate was washed with saturated NaCl, dried ($Na_2SO_4$) and evaporated to dryness to provide a thick oil. It was chromatographed on TLC grade $SiO_2$ (100 g) using 10% ethyl acetate in n-hexane as eluent. Fractions 103-135 (~5 ml each) gave pure 6R-alcohol. Yield: 0.6268 g.

Note: The 6(S)-alcohol of opposite configuration was obtained by substituting (+) α-pinene with (−) α-pinene in the above reaction.

PREPARATIVE EXAMPLE VII

2-PENTADECYNE 1-OL

A stirred solution of the aldehyde from preparative example II (16.56 g) in methanol (160 ml) and water (16 ml) was cooled (ice bath) and treated with $NaBH_4$ (1.25 g) in small portions. After ~10 minutes a crystalline precipitate separated. Stirring was continued for 30 minutes. The solvents were evaporated in vacuo and the residue was distributed between $CH_2Cl_2$ (~100 ml) and water (~50 ml). $CH_2Cl_2$ phase was separated and the aqueous phase extracted twice with $CH_2Cl_2$. The combined $CH_2Cl_2$ extracts were washed once with water, dried ($Na_2SO_4$) and evaporated to dryness to provide a crystalline solid, m.p. 36°-37° C. Yield: 17.8 g.

PREPARATIVE EXAMPLE VIII

1-BROMO-2-PENTADECYNE

A stirred solution of the alcohol (17 g; preparative example VII) in $CH_2Cl_2$ (500 ml) was treated with $CBr_4$ (30.19 g). After all $CBr_4$ had dissolved, the solution was cooled (ice bath) and treated with $Ph_3P$ (25.87 g). The reaction was worked up after 1 hour as follows: $CH_2Cl_2$ was evaporated in vacuo and the gummy residue treated with n-hexane. A precipitate of $Ph_3P=O$ so obtained was removed by filtration and washed with n-hexane. The combined filtrate and washings were evaporated to dryness in vacuo and passed through a column of coarse $SiO_2$ (200 g) using n-hexane (~2L) as eluent. Evaporation of the n-hexane eluate in vacuo (temp. 60°-90°) provided the bromide as a colorless oil. Yield: 19.9 g.

PREPARATIVE EXAMPLE IX

2-PENTADECYNE-1-TETRAMETHYLENE SULFONIUM BROMIDE

To a solution of the bromide (18.9 g.; preparative example VIII) in 150 ml methanol:water (9:1) was added tetrahydrothiophene (7.56 g). The reaction mixture was efficiently stirred for 2 days. After washing once with n-hexane, the MeOH:water phase was evaporated to dryness and the residue dissolved in $CH_2Cl_2$. The methylene chloride solution was concentrated to ~10 ml and treated with n-hexane until separation of colorless crystals took place. The crystals were collected by filtration. Yield: 13.6 g, m.p. 76°-79° C.

PREPARATIVE EXAMPLE X

TRANS-5,6-EPOXY-7-EICOSYNOIC ACID METHYL ESTER/CIS-5,6-EPOXY-7-EICOSYNOIC ACID METHYL ESTER

A stirred and cooled solution (bath temperature −25°) of the tetramethylene sulfonium bromide (3 g; preparative example IX) methyl 4-formylbutyrate (1.04 g) containing benzyltriethylammonium chloride (0.054 g) in $CH_2Cl_2$ (15 ml) was treated with 10M NaOH solution (8.06 ml) in one portion. The mixture was efficiently stirred for 1 min. and then rapidly cooled to −70°(bath temp.). $CH_2Cl_2$ layer was decanted out with a pippette. The frozen aqueous phase was washed 3–4 times with $CH_2Cl_2$, the combined $CH_2Cl_2$ extract and washings were washed with water, dried ($Na_2SO_4$) and evaporated to dryness to provide a turbid oil. The products from four such reactions were combined to yield 14.2 g total crude product which was chromatographed on TLC grade $SiO_2$. The column was eluted with 50% n-hexane/$CHCl_3$ (containing 2 ml/1L triethylamine) and ∼6 ml fractions were collected:
Fractions 102–132 Pure trans-epoxide
Fractions 191–205 Pure cis-epoxide

PREPARATIVE EXAMPLE XI

(±) METHYL 6-BROMO-7-EICOSYNOATE

This compound was prepared by reaction of methyl 6-(±)-hydroxy-7-eicosynoate (preparative example V) with $CBr_4$/$Ph_3P$ reagent in exactly the same manner as described in preparative example VIII. Note: By use of the corresponding 6-R, and 6-S alcohols (preparative example VI) the optically active (+) and (−) 6-bromo-7-eicosynoates were also obtained.

PREPARATIVE EXAMPLE XII

5,6-EPOXY-6-(1-TETRADECYNYL)UNDECANEDIOIC ACID, DIMETHYL ESTER 0.19 g. of the product from example 70 was cooled in ice bath and meta-chloroperbenzoic acid (0.07 g) was added. Additional 0.1 g peracid was added in two portions after two and three hours period. Two hours later, the reaction mixture was diluted with $CH_2Cl_2$ (180 ml), washed with aqueous $NaHSO_3$, aqueous $Na_2CO_3$ (3×50 ml), then with water and dried over $Na_2SO_4$. The reaction mixture was purified by column chromatography on silica gel ($CHCl_3$). The fractions containing the title compound were further purified by preparative thin layer chromatography on silica gel (20% EtOAc/hexanes). Yield: 0.139 g.

PREPARATIVE EXAMPLE XIII

(±)-DIPOTASSIUM 5,6-EPOXY-6-(1-TETRADECYNYL)-UNDECANEDIOATE 0.37 g. of 6-(1-tetradecynyl)-5,6-pooxy-undecandioic acid dimethyl ester was stirred at room temperature with 5 ml of absolute EtOH and 1.84 ml of 10% aqueous KOH for 24 hours. The solvents were then evaporated and the mixture was desalted on a XAD-4 resin (35 g) column. The column was eluted first with water to pH=7, then with 50% $H_2O$/MeOH to provide in methanolic fractions the title compound.

We claim:

1. A compound having the structural formula II or a pharmaceutically acceptable salt thereof,

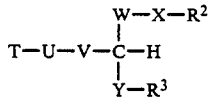

wherein
T is a straight or branched chain alkyl having from 7–15 carbon atoms which may optionally contain from 1–3 non-cumulative double or triple bonds;
U is —C≡C—;
V is a straight or branched chain alkylene having from 1 to 4 carbon atoms or is a direct bond;
W represents O or $S(O)_m$ wherein m is 0, 1 or 2;
X is a straight or branched chain alkylene having from 2 to 12 carbon atoms which may optionally contain from 1 to 3 non-cumulative double or triple bonds and which may be optionally substituted with a group —$NHR^a$ {wherein $R^a$ is hydrogen, alkyl having from 1 to 6 carbon atoms, $COCF_3$, $CO(CH_2)_2CH(NH_2)CO_2H$, or $SO_2R^b$ and wherein $R^b$ is alkyl having from 1 to 6 carbon atoms or $CF_3$};
Y represents straight or branched chain alkylene having from 1 to 12 carbon atoms which is substituted with the group $OR^c$ {wherein $R^c$ is hydrogen, carboxylic acyl having from 1 to 6 carbon atoms, tetrahydropyran-2-yl, or $COCH_2CH_2CO_2H$} and may optionally contain from 1 to 3 non-cumulative double or triple bonds; and
$R^2$ and $R^3$ may be the same or different and are independently selected from $CH_2OR^c$ {wherein $R^c$ is hydrogen, carboxylic acyl having from 1 to 6 carbon atoms, tetrahydropyran-2-yl or $COCH_2CH_2CO_2H$}, CHO, $COR^d$ {wherein $R^d$ is hydroxy, alkoxy having from 1 to 6 carbon atoms, $OCH_2OC(O)C(CH_3)_3$, or $NHR^e$ and wherein $R^e$ is hydrogen, alkyl having from 1 to 6 carbon atoms or $CH_2CO_2H$} or $SO_3H$, with the proviso that at least one of $R^2$ and $R^3$ is carboxyl.

2. The compounds defined in claim 1 wherein:
T is straight chain alkyl having from 7–15 carbon atoms;
V is a direct bond;
W is O or S;
X is a straight or branched chain alkylene having from 2 to 6 carbon atoms and Y is a straight or branched chain alkylene having from 2 to 6 carbon atoms which is substituted with the group $OR^c$ {wherein $R^c$ is hydrogen, carboxylic acyl having from 1 to 6 carbon atoms, tetrahydropyran-2-yl, or $C(O)CH_2CH_2CO_2H$}; and
$R^2$ and $R^3$ are COOH.

3. A compound defined in claim 2, having structural formula II wherein the substituents T-U-V- are combined to form the n-1-tetradecyn-1-yl group.

4. A compound defined in claim 1 having structural formula II wherein the substituents $R^2$ and $R^3$ may be the same or different and are $COR^d$ wherein $R^d$ is defined in claim 1.

5. A method for treating allergic reactions in a mammal which comprises administering an anti-allergic effective amount of a compound of formula II as defined in claim 1 to said mammal.

6. A method for treating inflammation in a mammal which comprises administering an anti-inflammatory effective amount of a compound of formula II as defined in claim 1 to said mammal.

7. A pharmaceutical composition which comprises a compound of formula II as defined in claim 1 in combination with a pharmaceutically acceptable carrier.

* * * * *